United States Patent
Lin et al.

(10) Patent No.: US 6,352,827 B1
(45) Date of Patent: Mar. 5, 2002

(54) DETECTION OF MULTIPLE NUCLEIC ACID SEQUENCES IN A FLUID SAMPLE

(75) Inventors: Edmund C. C. Lin, Boston, MA (US); Breck O. Parker, Keene, NH (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 08/908,494

(22) Filed: Aug. 7, 1997

Related U.S. Application Data (60) Provisional application No. 60/025,045, filed on Aug. 28, 1996.
(51) Int. Cl.[7] .............................. C12Q 1/70; C12Q 1/68; C12P 19/34; G01N 33/00
(52) U.S. Cl. .............................. 435/5; 435/6; 435/91.1; 436/94
(58) Field of Search .................. 435/6, 91.1, 183, 435/91.2, 7.2, 7.32, 320.1, 252.3; 436/94; 536/23.1, 24.3, 24.33, 25.3, 5

(56) References Cited

U.S. PATENT DOCUMENTS 5,679,510 A * 10/1997 Ray et al. .................. 435/5

* cited by examiner

*Primary Examiner*—Ethan Whisenant
*Assistant Examiner*—Frank Lu
(74) *Attorney, Agent, or Firm*—Peter F. Corless; Edwards & Angell, LLP (57) ABSTRACT

The present invention provides methods and kits for detection, and optionally quantitation, of multiple nucleic acid sequence analytes in a single fluid sample. The assays and kits of the invention employ a plurality of species of capture probes, each species comprising a bacteriophage covalently or non-covalently linked to an oligonucleotide complementary to one analyte, wherein the bacteriophage of each species is capable of generating a distinctive signal when plated on an indicator medium. The oligonucleotide moieties of each capture probe contain a sufficient number of contiguous ribonucleotides to confer sensitivity to a ribonuclease specific for RNA/DNA or RNA/RNA duplexes. In the method of the invention, the capture probe species are combined with the fluid sample, which has been processed to release single-stranded nucleic acids. Hybridization is allowed to occur, thereby generating DNA/RNA or RNA/RNA duplexes. By adding a nucleolytic enzyme capable of cleaving DNA-RNA duplexes, bacteriophage are released for detection of the different signals on an indicator medium. The kit of the invention provides components which allow the method of the invention to be performed.

34 Claims, 2 Drawing Sheets

DETECTION OF MULTIPLE NUCLEIC ACID SEQUENCES IN A FLUID SAMPLE

This application claims priority under 35 U.S.C. 119 (e) to U.S. provisional application No. 60/028,045, filed on Aug. 28, 1996.

The present invention relates to the field of assay for multiple nucleic acid sequence analytes in a single fluid sample. More particularly, the present invention is directed to detection, in a sample, of multiple nucleic acid sequence analytes, for example, those characteristic of pathogenic organisms or of oligonucleotide therapeutic agents, as an aid to diagnosis and treatment of disease states, or those characteristic of contaminants in reagents that are required to be sterile.

BACKGROUND OF THE INVENTION

Nucleic acid sequence-based assays can directly or indirectly measure the level of a analyte nucleic acid present in biological fluids. Many such assays are known, for example, as disclosed in U.S. Pat. Nos. 5,124,246; 4,775,619; 5,328,825; 5,232,829; and 5,283,174. Such assays generally rely on amplification, either of the nucleic acid analyte itself or of the signal generated by a probe. The amplification requirement inherent to currently available DNA sequence-based assays necessitates specialized equipment and training of laboratory personnel. When the nucleic acid analyte is amplified, as by the polymerase chain reaction, standardized results are generally not available, and the procedure is susceptible to contamination. Moreover, PCR amplification products often contain sequence inaccuracies. When the signal is amplified, high backgrounds can result from non-specific binding of the probe to non-analyte nucleic acids and to other species present in the sample.

Occasionally a single biological sample contains more than one clinically relevant nucleic acid analyte. For example, when any of a number of pathogens could cause similar symptomatology, or when an individual may be infected with more than one pathogen, separate assays must be performed for each pathogen. Oligonucleotide-based therapeutic agents are also used in clinical trials, and ultimately, an individual treated with a combination of such agents will require monitoring for their presence.

Using currently available methodologies, a separate assay must be performed for each nucleic acid analyte. The amount of biological sample required for such multiple assays is greater than that required for a single assay, necessitating increased handling, storage, and instrumentation in addition to potential increased patient discomfort. The requirement for separate assays for each nucleic acid analyte can increase the expense of diagnosis as well as the time involved in reaching diagnosis and thus in deciding on appropriate treatment.

Significant difficulties arise in using known nucleic acid sequence-based assays for simultaneous detection of more than one analyte nucleic acid in a biological sample. The presence of more than one probe sequence could result in cross-hybridization to PCR products that contain sequence inaccuracies. The high background problem in signal-amplification assays could interfere with detection of multiple signals. Thus a need exists for novel DNA-based diagnostics which accurately and efficiently detect multiple nucleic acid analytes, with minimal expense and inconvenience for clinician and patient.

Multiple DNA sequences on chromosomes have been detected simultaneously using the fluorescence in situ hybridization approach disclosed in P. M. Nederlof, et al. (1990), *Cytometry* 11, 126–131. In this method, alphoid and satellite DNA probes specific for human chromosomes were used to detect chromosomal aberrations. T. Ried, et al. (1992), *Proc. Natl. Acad. Sci. USA* 89, 1388–1392, expanded the fluorescence in situ hybridization technique through use of an epifluorescence microscope equipped with a digital imaging camera and computer software that allowed pseudocoloring and image merging. With this system it was possible to distinguish seven different probes using three fluorochromes. Although probe-based pathogen diagnosis is mentioned in Ried et al., the probes disclosed are limited to chromosome-specific alphoid DNAs and to probes containing sequences mapped to particular chromosomes. The probes of Ried et al. were capable of distinguishing different human chromosomes or of distinguishing the locus of a particular sequence on a single chromosome. Dirks et al. (1991) *Exp. Cell Research* 194, 310–315, discloses use of fluorochrome-labeled oligonucleotides in combination with oligonucleotides labeled with biotin-11-dUTP and digoxigenin-11dUTP for in situ hybridization studies of three closely related mRNAs.

SUMMARY OF THE INVENTION

The present inventors have discovered a method of assaying for multiple nucleic acid sequence analytes in a single fluid sample. The method of the invention distinguishes different nucleic acid sequence analytes present in a biological sample through use of a plurality of species of capture probes, each species comprising a bacteriophage linked to an oligonucleotide complementary to one analyte. Each bacteriophage is capable of generating a distinctive signal when plated on an indicator medium. In a preferred embodiment, the oligonucleotide moiety of each capture probe species contains a sufficient number of contiguous ribonucleotides to provide a DNA/RNA or RNA/RNA substrate when hybridization to nucleic acid sequence analytes occurs. In this embodiment, after hybridization to nucleic acid sequence analytes has occurred, the hybridization mixture is treated with a ribonuclease capable of cleaving DNA/RNA or RNA/RNA duplexes. In another embodiment, the oligonucleotide moieties of each capture probe species contains only deoxyribonucleic acids, and the hybridization mixture is treated with an appropriate restriction endonuclease to cleave DNA/DNA hybrids formed. Treatment of the hybrids with the ribonuclease or restriction endonuclease releases infective bacteriophage. Each species of capture probe may be detected, and optionally quantitated, by adding the bacteriophage to a bacterial host strain, allowing infection to proceed, and detecting the distinctive signals in bacteriophage plaques produced on an indicator medium. In this way multiple nucleic acid sequence analytes in a single biological sample may be detected.

In one embodiment, the invention provides an assay to detect at least two different nucleic acid sequence analytes in a fluid, comprising the steps of: processing the fluid to release single-stranded nucleic acids; providing at least two species of capture probes, each species comprising a bacteriophage linked to a single-stranded oligonucleotide complementary to one analyte, wherein the bacteriophage of each species is capable of generating a distinctive signal when plated on an indicator medium; combining the fluid and capture probes at a temperature and for a time sufficient to form a hybridization mixture without irreversibly destroying the infectivity of the bacteriophage; incubating the hybridization mixture with a nuclease capable of cleaving nucleic acid duplexes formed in the hybridization step, at a temperature and for a time sufficient to allow cleavage of said duplexes, thereby releasing infective bacteriophage; plating the infective bacteriophage on the indicator medium; and detecting the signals corresponding to the infective bacteriophage.

In another embodiment, the invention provides a kit comprising at least two species of capture probes, each species comprising a bacteriophage linked to a single-stranded oligonucleotide complementary to one analyte, wherein the bacteriophage of each species is capable of generating a distinctive signal when plated on an indicator medium.

DETAILED DESCRIPTION OF THE PREFERRED EMBODIMENTS

The assays and kits of the present invention allow rapid and cost-effective simultaneous detection, and optionally quantitation, of multiple nucleic acid analytes which differ in sequence from one another and thus are termed "nucleic acid sequence analytes". The assays and kits of the invention may be used for identification, and optionally for quantitation, of the organism or organisms which cause a particular disease state. The assays and kits of the invention may also be used to detect and optionally to quantitate multiple nucleic acids in a fluid sample. The number of capture probes to be included in each assay or kit is limited only by the number of bacteriophage signals that may be distinguished. Preferably, at least two species of capture probes are included in each assay or kit. More preferably, at least six species of capture probes are included in each assay or kit. Most preferably, from four to about ten species of capture probes are included in each assay or kit.

The particular nucleic acid sequence analytes to be detected in an assay in accordance with the invention are chosen by determining the clinical manifestation which the assay is intended to diagnose or monitor. For example, when the assay is used for diagnostic purposes, the nucleic acid sequence analytes correspond to organisms that may potentially cause a particular symptomatology. When the assay is used to detect oligonucleotide therapeutic agents, the analytes are chosen in accordance with the identity of the oligonucleotide therapeutic agents likely to be administered for treatment of a particular pathological state.

Any combination of nucleic acid sequence analytes may be detected using the methods and kits of the present invention. When the assay is used to detect and optionally to quantitate pathogenic organisms, individual DNA or RNA genomes, either double-stranded or single-stranded, may be detected. Any viral genome may be detected and optionally quantitated using the methods and kits of the present invention. For example, genomes of pox viruses, herpesviruses, adenoviruses, papova viruses, myxoviruses, retroviruses, arboviruses, picornaviruses, rabies viruses, rubella viruses, hepatitis viruses, and the like, may all be detected in accordance with the present invention. Similarly, any bacterial pathogen genome may be detected and optionally quantitated using the methods and kits of the present invention. Genomes of both gram-positive and gram-negative bacteria may be detected in accordance with the invention. Genomes of bacterial species from any genus, such as Staphylococcus, Pneumococcus, Streptococcus, Bacillus, Corynebacterium, Listeria, Neisseria, Treponema, Legionella, Clostridium, Mycobacterium, Streptomyces, Nocardia, Pasteurella, Brucella, Haemophilus, Bordatella, Salmonella, Escherichia, Shigella, Vibrio, Borrelia, Leptospira, Mycoplasma, Chlamydia, Rickettsia, and the like, may all be detected and optionally quantitated using the methods and kits of the present invention. Genomes of fungal pathogens may be detected and optionally quantitated in accordance with the present invention. Genomes of fungal species from any genus, for example Blastomyces, Cryptococcus, Candida, Coccidioides, Histoplasma, and the like, may all be detected and optionally quantitated using the methods and kits of the present invention. Genomes of protozoal pathogens may also be detected and optionally quantitated in accordance with the present invention. Genomes of protozoal pathogens from any genus, such as Entamoeba, Giardia, Trichomonas, Trypanosoma, Leishmania, Plasmodium, Toxoplasma, and the like, may each be detected and optionally quantitated using the methods and kits of the present invention. In short, any pathogenic agent which is shed into a biological fluid may be detected in accordance with the present invention.

The configuration of the assays and kits when used to detect pathogenic organisms may be determined as follows. The clinical symptomatology to be diagnosed is selected. For example, an assay or kit of the invention may be directed to diagnosis of upper respiratory infections, oral infections, pleuropulmonary infections, abdominal infections, urogenital infections, neurological infections, vascular infections, hematologic infections, dermal infections, ocular infections, musculo-skeletal infections, and the like. The most common etiologic agents for the chosen symptomatology are then identified, and capture probes for a plurality of these agents are included in the assay or kit. For example, one assay or kit for diagnosis of upper respiratory infections comprises at least two capture probe species for any or all of the following agents: *S. pyogenes, M. pneumoniae, H. influenzae,* influenza virus, coxsackie virus, and echovirus. Another assay or kit for upper respiratory infections comprises at least two capture probe species for any or all of the following agents: *C. diphtheriae, H. influenzae, S. pneumoniae, M. pneumoniae,* influenza virus, and respiratory syncytial virus. As another example, the assay or kit may be configured to diagnose sexually transmitted diseases (STDs). Such an assay or kit comprises at least two capture probe species for any or all of the following agents: *N. gonorrhoeae, C. trachomatis, T. pallidum,* human immunodeficiency virus, herpes simplex virus, and human papillomavirus. When subspecies of a pathogen can cause different clinical manifestations, as with strains of *C. trachomatis* or with strains of human papillomavirus, the assay or kit can be configured to distinguish such subspecies. Additional assays and kits may be configured for diagnosis of infections in specific populations, for example, in infants or in AIDS patients. Those of skill in the art will be able to determine a wide variety of assay and kit configurations in accordance with the invention, without undue experimentation.

Any fluid that may potentially contain nucleic acids may be assayed using the methods and kits of the invention. Such fluids include pulverized and suspended geological samples, reagents used to manufacture diagnostic and therapeutic agents, and the like.

Similarly, the presence of any combination of different oligonucleotide therapeutic agents may be detected and optionally quantitated in a biological fluid using the methods and kits of the present invention. As such oligonucleotide therapeutic agents become commercially available, the particular agents to be detected and optionally quantitated, and thus the configuration of the assay or kit of the invention, will be readily determinable by those of skill in the art.

Any biological fluid may be assayed using the method of the invention. As defined herein, a biological fluid may be serum, plasma, whole blood, urine, semen, vaginal secretions, saliva, nasal secretions, sputum, milk, lymphatic fluid, lacrimal secretions, sweat, cerebrospinal fluid, bone marrow, ascites, cell lysate, biopsy homogenate, culture supernatant, sewage, and the like. The biological fluid sample may be assayed neat or diluted. Moreover, after processing which will allow for release of nucleic acid sequence analytes, any tissue or organ in which a pathogen or other nucleic acid analyte is sequestered may be subjected to the methods and kits of the present invention. If necessary, hydrolytic enzymes such as nucleases or proteases will be inactivated, for example, by heating, in order to avoid subsequent interference with the assay system. In accordance with the invention, a tissue or organ sample which has been processed to release nucleic acid sequence analytes is defined as a biological fluid.

In the first step of the assay of the invention, the biological fluid is processed to release single-stranded nucleic acids, i.e., to denature any double-stranded nucleic acids and thereby to make them available for hybridization to the oligonucleotide moiety of the capture probe of the invention. Methods for processing biological fluids to expose nucleic acids are known. Such processing may encompass heating for a time and at a temperature sufficient to denature the nucleic acids in the fluid. In this embodiment, the capture probe is combined with the processed biological fluid prior to allowing the fluid to cool, so that hybridization to the capture probe may occur. Alternatively, such processing may encompass exposing the biological fluid to a denaturing agent, for example, an alkali such as sodium hydroxide. The kit of the invention may optionally contain reagents suitable for performing the processing step: for example, the denaturing agent may be provided as a component of diluent for the biological fluid.

In the next step of the invention, the biological fluid is combined with a plurality of species of capture probes, each species comprising a different bacteriophage and a different oligonucleotide complementary to a particular nucleic acid sequence analyte. As defined herein, a "different bacteriophage" is one which yields a distinctive signal when plated on an indicator medium. In accordance with the invention a "signal" is any detectable manifestation in the bacteriophage employed in the capture probe. Signal differences among bacteriophage may occur by virtue of different genetic markers present on the bacteriophage genome. For example, the bacteriophage of one capture probe species within an assay or kit may contain a gene or cDNA encoding luciferase; a bacteriophage of a second capture probe species may contain a gene or cDNA encoding β-galactosidase; a bacteriophage of a third capture probe species may contain a gene or cDNA encoding alkaline phosphatase; a bacteriophage of a fourth capture probe species may contain a gene or cDNA encoding lactic dehydrogenase; a bacteriophage of a fifth capture probe species may contain a gene or cDNA encoding succinic dehydrogenase; a bacteriophage of a sixth capture probe species may contain a gene or cDNA encoding horseradish peroxidase; a bacteriophage of a seventh capture probe species may contain a gene or cDNA encoding lactoperoxidase, and so forth. Any gene or cDNA may serve as a genetic marker in accordance with the invention, so long as it can be inserted into the chosen bacteriophage genome and so long as the bacteriophage viability is maintained. Since many bacteriophage allow insertion of large amounts of foreign DNA, the assays and kits of the invention provide significant flexibility in configuration with regard to signal differences among the bacteriophage of capture probe species. Alternatively, signal differences among the bacteriophage of capture probe species may result from differences in a plaque morphological characteristic such as size, mottled appearance, and the like.

Any virulent bacteriophage is suitable for use as a component of the capture probes of the invention. Preferably, bacteriophage which infect either *Bacillus subtilis, Lactococcus lactis,* non-pathogenic strains of Pseudomonas, non-pathogenic strains of Salmonella, or non-pathogenic strains of *Escherichia coli* may be employed. Examples of preferred bacteriophage that infect *Bacillus subtilis* are φ29, PZA, SP01 and SP82 and any derivatives thereof. Examples of preferred bacteriophage that infect *Lactococcus lactis* are φvML3 and φLC3 and any derivatives thereof. Examples of preferred bacteriophage that infect Pseudomonas are φCTX and Pf3 and any derivatives thereof. Examples of preferred bacteriophage that infect Salmonella are P22 and PSP3 and any derivatives thereof. Examples of preferred bacteriophage that infect *Escherichia coli* are the T-even phages, T3, T7, single stranded DNA phages, RNA phages, lambdoid phages and any derivatives thereof. More preferably, φ29, φLC3, φCTX, P22, T4 (a T-even phage), φX174 (a single-stranded DNA phage), R17 (an RNA phage), T7 or a lambdoid phage may be employed. Most preferably, the lambdoid phages λ, λvir, φ80, φ81, phage 21, phage 82, phage 424, phage 432, λimm434, λEMBL derivatives, and λgt derivatives are all suitable as components of the capture probes used in the assays and kits of the invention.

In accordance with the invention, a coat protein of the bacteriophage of the capture probe is covalently or noncovalently linked to a first site (i.e., nucleic acid residue) on an oligonucleotide. The linkage between the bacteriophage and the oligonucleotide occurs via any polypeptide present on the surface of the bacteriophage so long as the infectivity of the bacteriophage is not diminished. For example, any of the polypeptides present on the surface of the head of the bacteriophage, or any of the polypeptides present on the surface of the tail of the bacteriophage may act as the sites of linkage between the bacteriophage and the oligonucleotide. When a lambdoid bacteriophage is used in the capture probes of the invention, either of the two major head proteins of bacteriophage λ, gpD and gpE, or the major tail protein of bacteriophage λ, gpV, may serve as the specific site of linkage between the bacteriophage and the oligonucleotide. Similarly, polypeptides analogous to the bacteriophage λ proteins, which are present on other bacteriophages, may also act as the sites of linkage between the bacteriophage and the oligonucleotide. Examples of sites for attachment of oligonucleotides to bacteriophage other than λ are: gp9 (tail protein) or gp5 (head protein) of P22, and gp8 (major capsid protein) of φ29.

Alternatively, a modified bacteriophage λgpV protein, or a modified version of an analogous tail protein from another bacteriophage, may serve as the site of linkage between the bacteriophage and the oligonucleotide. Methods for introducing such modifications are set forth, for example, in copending U.S. Ser. No. 08/053,866, allowed U.S. Ser. No. 08/299,249, and U.S. Ser. No. 08/368,870, incorporated herein by reference. When a lambdoid bacteriophage is employed, the gpV protein is preferably modified as set forth in Example 1.

As set forth above, the capture probe used in the invention may comprise a bacteriophage covalently linked to an oligonucleotide. Chemical methods for effecting a covalent linkage between the bacteriophage and the oligonucleotide are set forth in copending U.S. Ser. No. 08/368,870.

Preferably, linkage between the bacteriophage and the oligonucleotide is non-covalent, wherein the oligonucleotide moiety of the capture probe is chemically linked to a first member of a noncovalent binding pair, which is in turn non-covalently linked to a second member of the non-covalent binding pair. A non-covalent binding pair in accordance with the invention includes vitamins and their specific binding proteins, receptors and their high affinity ligands, antibodies and their respective antigens, lectins and the carbohydrates to which they bind, and the like. The second member of the non-covalent binding pair is in turn chemically linked to the bacteriophage. The chemical linkages between the oligonucleotide moiety and first member of the non-covalent binding pair, and between the bacteriophage and second member of the non-covalent binding pair, may be covalent or, if affinity is sufficiently high, non-covalent.

In a preferred embodiment, the oligonucleotide is linked to a vitamin binding protein, such as streptavidin or avidin, and the bacteriophage is linked to an acceptor protein for a vitamin, such as biotin. The acceptor protein is displayed on the surface of the bacteriophage. Methods for effecting display of an exogenous protein on the surface of a bacteriophage are known. When a lambdoid bacteriophage is used in the capture probe, the acceptor protein is preferably attached to a gpV or gpD protein. Methods for attaching an exogenous protein to a lambdoid gpV protein are disclosed in the copending applications cited above, and in Maruyama, et al. (1994), *Proc. Natl. Acad. Sci. USA* 91, 8273–8277. Display of proteins attached to a lambdoid gpD protein are disclosed in Sternberg et al. (1995), *Proc. Natl. Acad. Sci. USA* 92, 1609–1613. When a lambdoid bacteriophage is employed in the capture probe, the acceptor protein is preferably a biotin acceptor protein attached to a gpV protein as set forth in Example 2.

The oligonucleotide moiety of each capture probe is complementary to one of the nucleic acid sequence analytes detected and optionally quantitated by the assay or kit. The oligonucleotide moiety of each capture probe used in the assay or kit of the invention is characterized by a nucleic acid sequence complementary to a nucleic acid sequence analyte such as a conserved region of a genome of a pathogenic agent or an oligonucleotide therapeutic agent. Preferably, the oligonucleotide moiety of each capture probe is complementary to about ten to about fifty nucleotides of a nucleic acid sequence analyte. More preferably, the oligonucleotide moiety of each capture probe is complementary to about twelve to about thirty nucleotides of a nucleic acid sequence analyte.

The oligonucleotide moiety of each capture probe may contain only deoxyribonucleic acid, and in this embodiment, nucleic acid sequence analyte/capture probe duplexes formed in accordance with the method of the invention are cleaved by endonucleases specific for DNA/DNA duplexes. Methods for constructing oligonucleotide probes containing restriction endonuclease recognition sites are set forth in copending U.S. Ser. No. 08/368,870.

In the preferred embodiment, the oligonucleotide moiety of each capture probe is an oligoribonucleotide or a hybrid oligonucleotide having both ribonucleotide and deoxyribonucleotide components. In this way sensitivity to a nuclease specific for DNA/RNA or RNA/RNA duplexes is conferred on the nucleic acid sequence analyte/capture probe duplexes formed in accordance with the method of the invention.

Preferably, the oligonucleotide moiety of the capture probe comprises from about ten to about 25 contiguous ribonucleotides between a 5' portion comprising a plurality of contiguous deoxyribonucleotides and a 3' portion comprising a plurality of contiguous deoxyribonucleotides. More preferably, the oligonucleotide moiety of the capture probe comprises about ten contiguous ribonucleotides between a 5' portion comprising a plurality of contiguous deoxyribonucleotides and a 3' portion comprising a plurality of contiguous deoxyribonucleotides.

When the capture probe is designed as a molecule complementary to a pathogen genome, a conserved region of a pathogen genome is chosen as the nucleic acid sequence analyte. Preferably, the region of pathogen genome chosen to design the capture probe is specific for the pathogen, as compared to other organisms or agents detected by the assay or kit. Any portion of a region of a genome which is conserved among a subspecies of a pathogenic organism may serve as a template for the oligonucleotide moiety of the capture probe used in the invention, so long as a sufficient number of consecutive conserved nucleotides are present to allow hybridization to occur between the oligonucleotide moiety and the pathogen genome. Identification of conserved, unique regions of pathogen genomes is within the level of skill in the art, since many pathogen genomes are known or are readily determinable, and conserved regions of such genomes are readily apparent by comparison with other pathogen genomes. In accordance with the invention, the pathogen genome may be embodied as a single-stranded or double-stranded DNA genome, an RNA genome, or as mRNA.

Any chemical portion of the oligonucleotide moiety may be modified in accordance with the invention, so long as the oligonucleotide moiety's ability to hybridize to the nucleic acid sequence analyte is preserved. Such modifications may be made to enhance the stability of the oligonucleotide moiety when exposed to the biological fluid. For example, the nucleotides of the oligonucleotide moiety may be linked via other than phosphodiester internucleoside linkages known in the art such as phosphorothioates, phosphorodithioates, phosphoramidates, carbamates, carbonates, phosphate esters, alkylphosphonates, alkylphosphonothioates, phosphoramidites, phosphate esters, acetamidates, carboxymethyl esters, carbonates, phosphate triesters, or the like. Alternatively, the nucleic acid base of the 3' terminus may be modified to include a sulfhydryl group, or the sugar moiety of the 3' terminus may be modified to contain a sulfhydryl group. The 5' terminus of the oligonucleotide may be modified so that the primary amino group is present on the phosphodiester backbone, the nucleic acid base or on the sugar. In addition, the sugar of any ribonucleotide in the oligonucleotide may be modified by having an arabinose instead of a ribose, or having a 2'-substitution such as a 2'-O-alkyl, 2'-O-aryl, 2'-O-allyl, 2'-halo, or 2'-amino substitution. Methods for preparing such modifications of nucleic acids are well known in the art, as set forth, for example, in Uhlmann et al., (1990) *Chem. Rev.* 90, 543–584, in *Protocols for Oligonucleotides and Analogs,* Methods in Molecular Biology, vol. 20, *S. Agrawal,* ed. (Humana Press, Totowa, N.J. 1993) and in *Protocols for Oligonucleotide Conjugates,* Methods in Molecular Biology, vol. 26, S. Agrawal, ed. (Humana Press, Totowa, N.J. 1993). Such modified oligonucleotides are also commercially available, for example, from Integrated DNA Technologies, Inc., Coralville, Iowa.

In addition, modifications can occur at internal bases and sugars and on the phosphodiester backbone at positions other than the 5' terminal phosphate, so long as the oligonucleotide moiety's ability to hybridize to the nucleic acid sequence analyte is preserved. For example, phosphorothioate diesters can be incorporated into the phosphate backbone of the oligonucleotide at any position. Phosphothioate diesters can by alkylated with reagents containing γ-bromo-α,β-unsaturated carbonyls, iodo- or bromo-acetamides, or aziridinylsulphonamides to produce phosphorothioate triesters (Conway et al. (1991) in *Oligonucleotides and Analogues: A practical approach, Eckstein* (ed.), Oxford University Press, New York, pp. 211–239). In another example, modified pyrimidine nucleosides can be incorporated into the oligonucleotide. Such modifications include modifications of the C-5 position of 2'-deoxyuridine and modifications of the $N^4$ of 2'-deoxycytodine, as described by Ruth (1991) in *Oligonucleotides and Analogues: A practical approach, Eckstein* (ed.), Oxford University Press, New York, pp. 255–282.

In accordance with the invention, the oligonucleotide moiety of the capture probe is also modified to permit covalent or non-covalent linkage to a solid support or matrix at a functional group present on a first nucleic acid residue or site of the oligonucleotide. Any nucleic acid residue present on the oligonucleotide moiety may serve as a site for linkage to the solid support or matrix, so long as the availability of the oligonucleotide for hybridization to the nucleic acid sequence analyte is preserved. In accordance with the invention, the oligonucleotide may be attached directly to the solid support or matrix, or it may be attached to a linking molecule which is in turn attached directly to the solid support or matrix. In accordance with the invention, the oligonucleotide may be attached covalently or noncovalently to the linking molecule. Any linking molecule is suitable to attach the oligonucleotide to the solid support or matrix, so long as the linking molecule can maintain an attachment between the oligonucleotide and the solid support or matrix which is maintained during hybridization of the capture probe to the nucleic acid sequence analyte. Alternatively, the oligonucleotide may be covalently attached to the solid support or matrix, for example, through a thiol group incorporated in the oligonucleotide. One such example has been described by Blanks and McLaughlin (1991) in *Oligonucleotides and Analogues: A practical approach,* Eckstein (ed.), Oxford University Press, New York, pp. 241–254.

Any solid support or matrix is suitable for use in the present invention. For example, polypropylene resins, polystyrene resins, and the like are suitable as matrix components of the composition of the invention. Any membrane or bead designed for covalent or noncovalent attachment of molecules through primary amino groups is also suitable as a matrix in accordance with the present invention. A wide variety of beads or microspheres suitable for attachment to the oligonucleotide is commercially available. Microtiter plates of any material are also suitable solid supports in accordance with the invention. Methods are known for covalent and non-covalent attachment of free oligonucleotides to a variety of solid supports, for example, as set forth in EP 439,222 and EP 455,905.

As set forth above, the capture probes used in the assay and kits of the invention comprise an oligonucleotide moiety covalently or non-covalently linked at one terminus to a bacteriophage and covalently or non-covalently linked at the other terminus to a solid support or matrix. Any method may be employed to attach the oligonucleotide moiety to the bacteriophage, so long as the method allows attachment of preferably only one oligonucleotide per bacteriophage, and so long as infectivity of the bacteriophage is not irreversibly destroyed.

To maintain the sensitivity of the method of the invention it is necessary that each bacteriophage be linked to only one oligonucleotide moiety, since attachment of more than one oligonucleotide moiety to the bacteriophage will alter the probability of detecting some of the nucleic acid sequence analytes. When more than one oligonucleotide moiety is attached to the bacteriophage, more than one analyte may hybridize to each bacteriophage. In this situation, the probability that uncleaved duplexes, and thus noninfective bacteriophage, may continue to exist after treatment with the nuclease is high, and the sensitivity of the assay is likely to be altered. For each capture probe species, the number of oligonucleotide moieties linked to each bacteriophage may be controlled, for example, by using a limiting concentration of oligonucleotide moieties as compared to the concentration of bacteriophage, thus controlling the spacing of oligonucleotide on the bacteriophage surface. In this way the concentrations of oligonucleotide and bacteriophage may be adjusted so that the probability that one bacteriophage will be linked to two oligonucleotides is minimized. Alternatively, the concentration of oligonucleotide moieties on the solid support or matrix may be maximized in such a way that steric hindrance prevents attachment of more than one bacteriophage to each solid support or matrix. A third means for controlling the number of oligonucleotide moieties linked to each bacteriophage is to reduce the number of possible sites for linkage on the bacteriophage surface. When the linkage between oligonucleotide and bacteriophage is noncovalent, this may be accomplished by reducing the number of chemical linkages between the bacteriophage and the second member of the noncovalent binding pair. Use of a genetically modified bacteriophage such as the λVAS bacteriophage described in Example 3, in combination with biotin and an oligonucleotide moiety attached to avidin or streptavidin, permits optimal control of the number of oligonucleotides per bacteriophage.

Urdea et al. (*Nucleic Acids Res.* 16: 4937–4956, 1988) describe methods for covalently attaching the protein enzymes horseradish peroxidase and alkaline phosphatase to $N^4$-alkylamino deoxycytidine-containing oligodeoxyribonucleotides. In general, any heterobifunctional cross-linker or homobifunctional cross-linker such as those available from Pierce (Rockford, Ill.) can be employed to cross-link a protein to an oligonucleotide containing a functional group which reacts with the cross-linking reagent. In the aforementioned example, the $N^4$-alkyamino group reacts with the cross-linking reagent, diisothiocyanate. Such chemicals include, without limitation, N-(7dimethylamino-4-methylcoumarinyl)-maleimide; 5,5'-dithiobis(2-nitrobenzoic acid); 3-(N-maleimidopropionyl)-biocytin, and the like. Other chemicals may also be used to attach the oligonucleotide to the second member of the non-covalent binding pair, for example, those disclosed in Yamamoto, et al., *Anal. Biochem.* (1978) 84, 313–318; Zelakowski, *Anal. Biochem* (1980) 103, 307–312; and Bayer et al., *Methods Enzymol.* (1990) 184, 138–160. Generally, the method of attachment of the oligonucleotide moiety to the proteinaceous member of the binding pair will employ a large excess of the number of proteinaceous molecules over the number of oligonucleotide molecules.

In accordance with the invention, the above-described capture probes are combined with a sample of a fluid which may contain a plurality of nucleic acid sequence analytes, and the combination is incubated at a temperature and for a time sufficient to allow nucleic acid hybridization to occur, thereby forming a nucleic acid hybridization mixture. The conditions of the incubation must be such that the infectivity of the bacteriophage is preserved. Generally, incubation conditions for nucleic acid hybridization are well known, requiring relatively high temperatures and high salt concentrations, for example, for "stringent" hybridization. Because of the need to avoid irreversibly destroying the infectivity of the lambdoid bacteriophage moiety of the capture probe, the hybridization incubation conditions may be modified by addition of appropriate salts or by addition of polyamines, or the like, to allow hybridization to proceed efficiently at less than optimal hybridization temperatures. Additionally, ions may be required to maintain bacteriophage viability. Finally, the pH of the hybridization buffer is important for stability of the hybrid and viability of the bacteriophage. A preferred range is from pH 7.0 to 8.0. Such determinations of optimal hybridization conditions are routine for those of skill in the art.

In accordance with the method of the invention, after a time sufficient to allow substantially all of the nucleic acid sequence analytes present in the biological fluid to hybridize to the appropriate capture probes, the hybridization mixture is combined with nuclease capable of cleaving the nucleic acid duplexes that have been formed. When the oligonucleotide moiety of the capture probe comprises only deoxyribonucleic acid, such a nuclease may be an appropriate restriction endonuclease, as is described in detail in copending U.S. Ser. No. 08/368,870. In the preferred embodiment, each of the capture probes contains a number of contiguous ribonucleotides sufficient to form a substrate for an endoribonuclease that cleaves RNA/RNA duplexes, such as RNase III, or to form a substrate for a ribonuclease that cleaves DNA/RNA duplexes, such as RNase H. The nuclease is incubated with the duplexes at a temperature and for a time sufficient to allow cleavage of all duplexes present. Such incubation conditions are readily determinable for nucleolytic enzymes.

Infective bacteriophage are released by the action of the nuclease, and the different signals generated by each species of capture probe may be detected by plating the bacteriophage on an indicator medium. As is well known in the art, "plating" is defined as incubating an aliquot of the bacteriophage with an aliquot of a suitable bacterial host for a time sufficient to allow infection by the released bacteriophage, depositing this mixture at a suitable dilution on an indicator medium, and incubating the diluted mixture for a time and at a temperature sufficient to allow detectable plaque formation. In accordance with the invention, the dilution of combined bacteriophage and bacterial host is adjusted so that each bacteriophage yields a separate plaque which is not fused with other plaques when plated. Methods for obtaining distinct bacteriophage plaques are well known in the art.

Detection may be visual or microscopic, and when microscopic detection is used, a device for computer generation of images may be used. In accordance with the invention, an "indicator medium" is defined as a bacterial host and the culture medium on which the host is grown. Any bacterial host is suitable for performing this step of the method of the invention, so long as the host is not restricted for growth of the bacteriophage moiety of the capture probe species. Preferably, the bacterial host is deficient in one or more marker genes. Many such marker genes have been identified since bacteriophage studies began during the 1940's. For example, if the host is deficient (preferably deleted) for expression of a plurality of enzymatic markers such as β-galactosidase, alkaline phosphatase, lactic dehydrogenase, succinic dehydrogenase, and the like, bacteriophage of each capture probe species may be manipulated to contain and to constituently express an appropriate enzymatic marker. As set forth above, marker genes or cDNAs from non-bacterial genera, e.g., horseradish peroxidase, lactoperoxidase, luciferase, and the like, may also be introduced into the bacteriophage for use in accordance with the invention.

When grown in the presence of substrates for the enzymatic markers, the plaques generated by each species of capture probe will contain the appropriate enzyme and thus catalysis of the corresponding substrate will occur. The indicator medium used in the assays and kits of the invention thus contains a substrate for each enzyme produced by bacteriophage of each capture probe species. Each substrate yields a different signal, since each plaque will contain progeny of a single bacteriophage. In accordance with the invention, the plaques are analyzed for the presence of each signal. Such analysis may be visual, if the plaques are allowed to develop to a sufficiently large size, e.g., by overnight incubation. Alternatively, earlier detection of chromogenic or fluorescent signals may be accomplished by including more bacteria in the plating mixture and by using microscopic detection methods. When the bacteriophage contain a fluorescent signal, microscopic detection is preferred. Multiple fluorescent signals may be detected in accordance with the invention using an epifluorescence microscope coupled to a cooled charge coupled device (i.e., camera), for example, as described in Ried et al., supra.

The method of the invention may be performed manually, or it may be automated. In one automated embodiment of the method of the invention, the capture probes are bound to polystyrene wells of a microtiter plate using known methods. For example, attachment of the capture probes to the microtiter plate may be performed using a plate coating system, such as the Dynatech Autoprocessor (Dynatech Laboratories, Inc., Chantilly, Va.).

The present invention may also be embodied as a kit for detection and optionally quantitation of nucleic acid sequence analytes in a biological fluid. The kit of the invention includes the capture probe species described above, along with such other components as allow practice of the method of the invention. For example, buffers for enhancing the hybridization reaction of the method of the invention may be provided as kit components. An indicator medium for plating the bacteriophage may also be included for example, such selective medium may comprise a suitable bacterial host and a plating composition comprising the various substrates catalyzed by the enzymatic marker contained within the bacteriophage of each capture probe species. An endoribonuclease capable of cleaving RNA/DNA duplexes such as RNase H, or an endoribonuclease capable of cleaving RNA/RNA duplexes such as RNase III, or a restriction endonuclease may also be provided as a kit component. Buffers suitable for the enzyme reactions employed in the method may also be included in the kit of the invention. When colorimetric, fluorescent or luminescent methods are used to detect the number of bacteriophage released from the matrix, reagents suitable for performing the colorimetric, fluorescent, or luminescent methods such as enzymes or substrates may be included as kit components. Additional kit components may also be included which enhance the convenience of the assay, for example, assay tubes, pipette tips, Petri dishes, and the like.

The following examples illustrate the preferred modes of making and practicing the present invention, but are not meant to limit the scope of the invention since alternative methods may be used to obtain similar results.

EXAMPLE 1

λgpV Fusion Constructs

The 4.58 kb BamHI/APAI restriction fragment containing λphage gene V was subcloned from λgt11 into pLITMUS 38

(New England Biolabs, Beverly, Mass.). This served as the λ shuttle vector, pHS1, allowing specific DNA sequences to be moved back into λ.

Polymerase chain reaction (PCR) cloning techniques were used to amplify the 1.3S transcarboxylase gene of *P. shermanii* and gene V of λ phage gt11. An amber stop codon (TAG) was inserted at either of two positions of gene V; TAG was substituted for $CAG^{gln177}$ and $CAG^{glu234}$, and are referred to as $V^{am177}$ and $V^{am234}$ respectively. A unique SfiI site was introduced prior to the start of the coding region for the 1.3S subunit and immediately following each amber codon in gene V. Gene V and the 1.3S transcarboxylase subunit were simultaneously cloned into the pKK223-3 expression vector (Pharmacia) after digesting gene V with EcoRI/SfiI and the transcarboxylase gene with SfiI/Hind III. The PT-box, formed by annealing two complementary 81 base oligonucleotides containing the Pro-Thr DNA sequence data, was inserted into the SfiI site to complete the gpV-PT 1.3S transcarboxylase gene fusion construct. The gene fusion constructs containing $V^{am177}$ and $V^{am234}$ referred to as pHS4 and pHS5 respectively.

The 15 base intergenic DNA sequence between gpV-PT-1.3S and Gene G of λ phage was modified to create a HindIII restriction site. To create this site, bases TCC at positions 9696–9698 in λ gt11 were replaced with GCTT using PCR cloning techniques. The AatII/HindIII gpV-PT-1.3S restriction fragments were subcloned simultaneously with the HindIII/ApaI gene G fragment into pHS1. The gene fusion-gene G constructs containing $V^{am177}$ and $V^{am234}$ are referred to as pHS6 and pHS7 respectively.

EXAMPLE 2

Expression of Fusion Constructs

*E. coli* strain XL1-blue was transformed with each of the fusion constructs, pHS4 and pHS5. The fusion proteins were IPTG induced, whole cell lysates were loaded onto a 15% SDS-PAGE gel and coomassie blue stained, and analyzed for biotinylation of the 1.3S fusion moiety by Western analysis-streptavidin conjugated alkaline phosphatase. The results showed expression of both the truncated version of each gene V ($V^{am177}$ and $V^{am234}$) and the full length fusion construct, gpV-PT-1.3S. Western analysis showed that each fusion construct acted as an acceptor protein for biotin via *E. coli* biotin ligase.

EXAMPLE 3

Construction of λVAS

Figure 1:
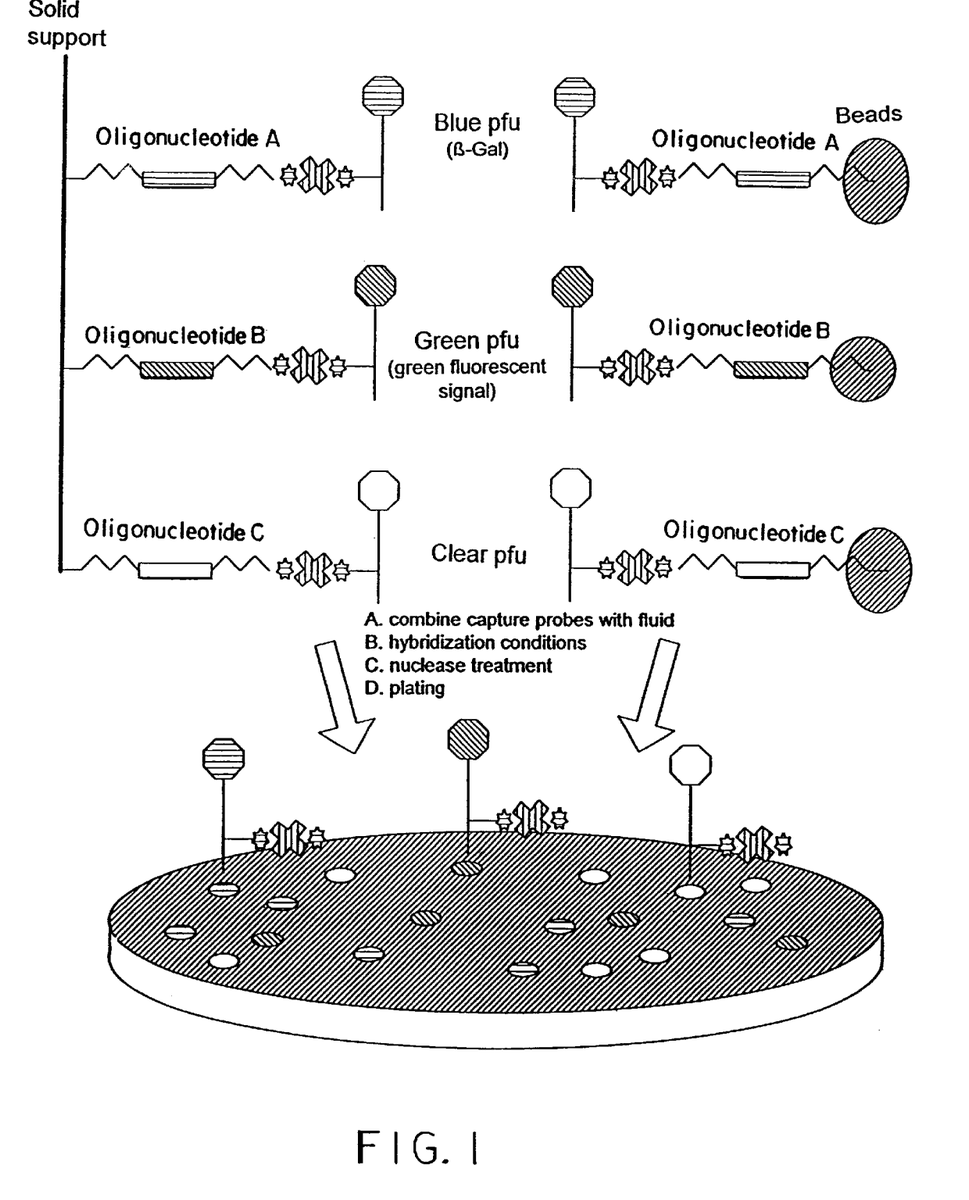
FIG. 1 shows a schematic depiction of the method of the invention.
Figure 2:
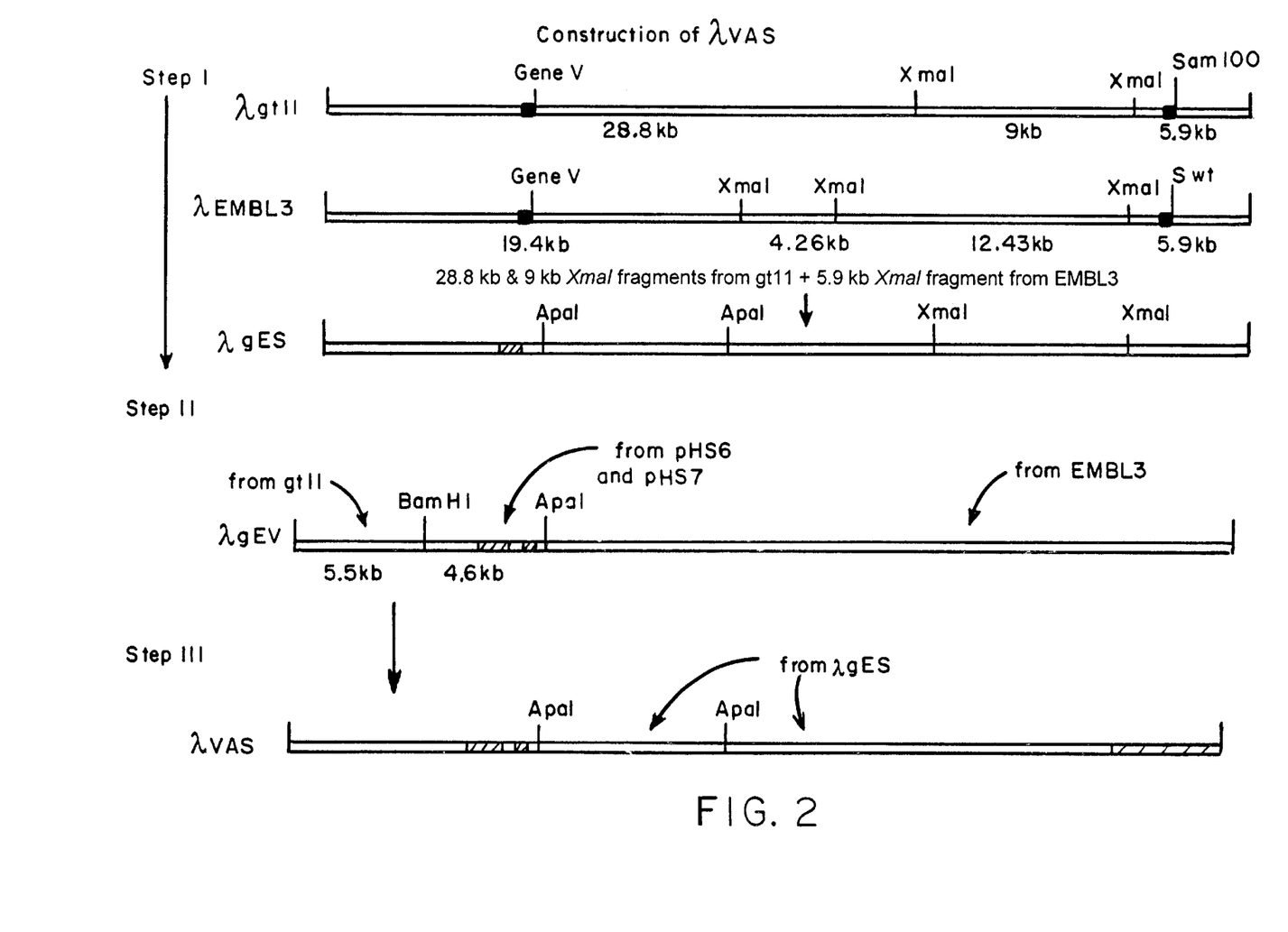
FIG. 2 shows a schematic depiction of the cloning strategy set forth in Example 3.

These experiments are schematically depicted in FIG. 2. The 5.9 XmaI fragment of λ gt11 carrying the Sam100 mutation was replaced with the same fragment from λ-EMBL3 carrying the wild type gene S. This phage is referred to as λgES (gt11 with Swt). The BamHI/ApaI λgp-V-PT-1.3S fusion fragments from pHS6 and pHS7 were subcloned into the same sites of λ-EMBL3. These recombinant phage are referred to as $\lambda gEV^{am177}$ and $\lambda gEV^{am234}$. The ApaI left-arm fragment from λgEV was ligated to the two ApaI -right-arm fragments of λgES to produce the complete recombinant phage, λVAS(λVAS-177 and λVAS-234). Construction was confirmed through plaque hybridizations and restriction analysis of λVAS DNA. Western analysis showed that the gpV-PT-1.3S fusion protein was expressed under λ control and efficiently biotinylated.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. An assay to detect at least two different nucleic acid sequence analytes in a fluid, comprising the steps of:
    a) processing the fluid to release single-stranded nucleic acids;
    b) providing at least two species of capture probes, each species comprising a bacteriophage linked to a single-stranded oligonucleotide complementary to one analyte, wherein the bacteriophage of each species is capable of generating a distinctive signal when plated on an indicator medium;
    c) combining the fluid and capture probes at a temperature and for a time sufficient to form a hybridization mixture without irreversibly destroying the infectivity of the bacteriophage;
    d) incubating the hybridization mixture with a nuclease capable of cleaving nucleic acid duplexes formed in step c, at a temperature and for a time sufficient to allow cleavage of said duplexes, thereby releasing infective bacteriophage;
    e) plating the infective bacteriophage on the indicator medium; and
    f) detecting the signals corresponding to the infective bacteriophage.

2. The assay of claim 1, wherein the fluid is selected from the group consisting of serum, plasma, whole blood, urine, semen, vaginal secretions, saliva, sputum, milk, lymphatic fluid, sweat, lacrimal secretions, cerebrospinal fluid, bone marrow, ascites, cell lysate, biopsy homogenate, culture supernatant, and sewage.

3. The assay of claim 1, wherein the signal is selected from the group consisting of a chromogenic substance, a fluorescent substance, plaque morphology, a radioactive substance, and combinations thereof.

4. The assay of claim 1, wherein the signals are detected visually, spectrophotometrically, or microscopically.

5. The assay of claim 1, wherein a surface polypeptide of the bacteriophage is linked to a first site on the oligonucleotide.

6. The assay of claim 5, wherein the polypeptide is non-covalently linked to the first site.

7. The assay of claim 5, wherein the polypeptide is covalently linked to the first site.

8. The assay of claim 5, wherein a second site of the oligonucleotide is linked to a solid support.

9. The assay of claim 8, wherein the second site is non-covalently linked to the support.

10. The assay of claim 8, wherein the second site is covalently linked to the support.

11. The assay of claim 8, wherein the solid support is selected from the group consisting of a matrix, a bead, a membrane, and a microtiter plate.

12. The assay of claim 1, wherein at least three different nucleic acid sequence analytes are detected.

13. The assay of claim 1, wherein at least four different nucleic acid sequence analytes are detected.

14. The assay of claim 1, wherein at least five different nucleic acid sequence analytes are detected.

15. The assay of claim 1, wherein at least six different nucleic acid sequence analytes are detected.

16. The assay of claim 1, wherein the oligonucleotide comprises deoxyribonucleotides.

17. The assay of claim 16, wherein the nuclease is a restriction endonuclease.

18. The assay of claim 16, wherein the oligonucleotide further comprises ribonucleotides.

19. The assay of claim 18, wherein the nuclease is a ribonuclease.

20. A kit comprising at least two species of capture probes, each species comprising a bacteriophage linked to a single-stranded oligonucleotide complementary to one analyte, wherein the bacteriophage of each species is capable of generating a distinctive signal when plated on an indicator medium.

21. The kit of claim 20, further comprising an indicator medium.

22. The kit of claim 20, wherein the signal is selected from the group consisting of a chromogenic substance, a fluorescent substance, plaque morphology, a radioactive substance, and combinations thereof.

23. The kit of claim 20, wherein the signals are detected visually, spectrophotometrically, or microscopically.

24. The kit of claim 20, wherein a surface polypeptide of the bacteriophage is linked to a first site on the oligonucleotide.

25. The kit of claim 24, wherein the polypeptide is non-covalently linked to the first site.

26. The kit of claim 24, wherein the polypeptide is covalently linked to the first site.

27. The kit of claim 24, wherein a second site of the oligonucleotide is linked to a solid support.

28. The kit of claim 27, wherein the second site is non-covalently linked to the support.

29. The kit of claim 27, wherein the second site is covalently linked to the support.

30. The kit of claim 27, wherein the solid support is selected from the group consisting of a matrix, a bead, a membrane, and a microtiter plate.

31. The kit of claim 20, wherein at least three different nucleic acid sequence analytes are detected.

32. The kit of claim 20, wherein at least four different nucleic acid sequence analytes are detected.

33. The kit of claim 20, wherein at least five different nucleic acid sequence analytes are detected.

34. The kit of claim 20, wherein at least six different nucleic acid sequence analytes are detected.

\* \* \* \* \*